(12) United States Patent
Sumitani et al.

(10) Patent No.: US 6,703,245 B2
(45) Date of Patent: Mar. 9, 2004

(54) OXYGEN DETECTING COMPOSITION

(75) Inventors: Makoto Sumitani, Tokyo (JP); Haruo Inoue, Tokyo (JP); Ken Sugito, Chiba (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/277,959

(22) Filed: Oct. 23, 2002

(65) Prior Publication Data

US 2003/0082823 A1 May 1, 2003

(30) Foreign Application Priority Data

Oct. 26, 2001 (JP) .................................... 2001/329557
May 14, 2002 (JP) .................................... 2002/138427

(51) Int. Cl.$^7$ ............................................. G01N 31/22
(52) U.S. Cl. ........................... 436/136; 436/8; 436/127; 436/138; 436/164; 436/166; 436/169; 436/904; 422/55; 422/56; 252/408.1
(58) Field of Search ...................... 436/8, 127, 136, 436/138, 164, 166, 169, 904; 252/408.1; 422/55, 56

(56) References Cited

U.S. PATENT DOCUMENTS

| 3,950,180 | A | | 4/1976 | Kato | |
|---|---|---|---|---|---|
| 4,169,811 | A | * | 10/1979 | Yoshikawa et al. | 436/138 |
| 4,349,509 | A | * | 9/1982 | Yoshikawa et al. | 422/57 |
| 4,526,752 | A | * | 7/1985 | Perlman et al. | 422/56 |
| 5,096,813 | A | * | 3/1992 | Krumhar et al. | 435/28 |
| 5,358,876 | A | * | 10/1994 | Inoue et al. | 436/136 |

FOREIGN PATENT DOCUMENTS

| JP | 54-48294 | * | 4/1979 |
|---|---|---|---|
| JP | 56-42138 | * | 4/1981 |
| JP | 56-54354 | * | 5/1981 |
| JP | 56-84772 | * | 7/1981 |
| JP | 56-084774 | | 7/1981 |
| JP | 58-208354 | | 12/1983 |
| JP | 60-080763 | | 5/1985 |

* cited by examiner

*Primary Examiner*—Maureen M. Wallenhorst
(74) *Attorney, Agent, or Firm*—Antonelli, Terry, Stout & Kraus, LLP

(57) ABSTRACT

The oxygen detecting composition of the present invention includes a layered silicate, a cationic surfactant, an organic colorant, a reducing agent, and optionally a basic substance. The oxygen detecting composition is suitable for indicating the presence or absence of oxygen or the degree of oxygen concentration by its reversible color change because of its high light resistance, high heat resistance, transparency and translucency.

10 Claims, No Drawings

OXYGEN DETECTING COMPOSITION

BACKGROUND OF THE INVENTION

1. Field of the Invention

The present invention relates to an oxygen detecting composition, more particularly, relates to an oxygen detecting composition capable of indicating the presence or absence of oxygen or the degree of oxygen concentration by its color change, and exhibiting a good light and heat stability. The present invention further relates to an oxygen detecting agent and an oxygen detecting ink pigment each comprising the oxygen detecting composition.

2. Description of the Prior Art

Hitherto, there have been proposed oxygen detecting agents utilizing the reversible color change of organic colorants by oxidation-reduction reaction. For example, Japanese Patent Application Laid-Open Nos. 53-117495 and 53-120493 disclose solid oxygen detecting agents comprising an organic colorant such as thiazine dye, azine dye and oxazine dye, a reducing agent and a basic substance. Japanese Patent Application Laid-Open No. 56-84772 discloses an oxygen indicator ink composition prepared by dissolving or dispersing a thiazine dye or the like together with a reducing sugar and an alkaline substance into a resin solution. A commercially available oxygen detecting agent (for example, "AGELESS EYE", trademark of Mitsubishi Gas Chemical Company, Inc.) is a functional product for indicating a deoxygenated condition (oxygen content of less than 0.1% by volume) of a transparent packaging container in a simple manner by its color change, and has been used together with an oxygen-absorbing agent (for example, "AGELESS", trademark of Mitsubishi Gas Chemical Company, Inc.) to maintain a freshness of foods and to prevent the degradation of medical and pharmaceutical products.

The conventional oxygen detecting agent, however, is insufficient in the light and heat resistance, for example, tends to cause discoloration or deterioration in color change function upon exposure to light as well as cause browning or deterioration in color change function under high temperatures. To maintain its clear color for a long period of time, therefore, the conventional oxygen detecting agent must be stored by screening from light at low temperatures. This tendency is remarkable in case of a printed oxygen detecting agent comprising an ink having an oxygen detecting function.

In addition, the conventional oxygen detecting agent is opaque to hide the packaged contents such as foods, medical products and pharmaceutical products, thereby unfavorably making the contents invisible outwardly.

SUMMARY OF THE INVENTION

An object of the present invention is to provide a light-resistant and heat-resistant oxygen detecting composition and an oxygen detecting agent. Another object of the present invention is to provide a transparent or translucent solid oxygen detecting agent and an oxygen detecting ink pigment.

As a result of extensive research, the inventors have found that an oxygen detecting composition comprising a composite material prepared by mixing a layered silicate (sheet silicate), a cationic surfactant, an organic colorant, a reducing agent and an optional basic substance is excellent in the heat resistance and the light resistance. The inventors have further found that an oxygen detecting agent and an oxygen detecting ink pigment each comprising a composite material of a layered silicate intercalated with a cationic surfactant, an organic colorant, a reducing agent and an optional basic substance is not only excellent in the light resistance and the heat resistance, but also transparent or translucent. The present invention has been accomplished on the basis of these findings.

DETAILED DESCRIPTION OF THE INVENTION

The oxygen detecting composition according to the present invention contains, as the essential constituting components, a cationic surfactant, an organic colorant, a reducing agent and a layered silicate (sheet silicate), or a cationic surfactant, an organic colorant, a reducing agent, a basic substance and a layered silicate. Preferably, the cationic surfactant, the organic colorant, the reducing agent and the optional basic substance are intercalated into the layered silicate.

The cationic surfactants usable in the present invention are those having cationic atoms and lipophilic groups in their molecules, and being capable of generating organic cations in water by ionization. As the cationic surfactant, a quaternary ammonium salt is typically mentioned, with a quaternary ammonium salt having four carbon groups including at least one lipophilic group bonded to the nitrogen atom being preferred.

The lipophilic group means a non-polar atomic group having a strong affinity for oil, but less interacting with water. Examples of the lipophilic group include chain- and cyclic hydrocarbon groups, aromatic hydrocarbon groups, halogenated alkyl groups, organosilicone groups, and fluorocarbon groups.

The cationic surfactant is preferably cetyltrimethylammonium bromide, cetyltrimethylammonium chloride, stearyltrimethylammonium chloride, stearyltri(methylbenzyl) ammonium chloride, distearyldimethylammonium chloride, or distearyldi(methylbenzyl)ammonium chloride.

The organic colorant usable in the present invention is an aromatic compound having a long conjugated double bond system containing mobile π electrons, and is capable of reversibly changing its color by oxidation-reduction reaction. Examples of the organic colorant include oxidation-reduction indicators, thiazine dyes, azine dyes, oxazine dyes, indigoid dyes, and thioindigoid dyes. Specific examples include methylene blue, new methylene blue, methylene green, variamine blue B, diphenylamine, ferroin, capri blue, safranine T, indigo, indigo carmine, indigo white, and indirubin. Of these, preferred are triazine dyes represented by methylene blue.

The reducing agent used in the present invention is a compound capable of reducing the organic colorant in an atmosphere having an oxygen concentration lower than that of atmospheric air. Examples of the reducing agents include monosaccharides such as glucose, fructose and xylose; reducing disaccharides such as maltose; ascorbic acid and its salts; dithionous acid and its salts; and cysteine and its salts.

In some cases, it is preferred to combinedly use the basic substance to enhance the reduction activity of the reducing agent. As the basic substance, there may be used hydroxides such as sodium hydroxide, potassium hydroxide and calcium hydroxide; and carbonates such as sodium carbonate, potassium carbonate and sodium hydrogen carbonate. The amount of the basic substance, if used, is preferably 0.001 to 10 parts by weight, more preferably 0.01 to 1 part by weight based on one part by weight of the layered silicate.

The layered silicate (sheet silicate) used in the present invention has a layered structure that comprises a number of sheets repeatedly stacked in parallel, each sheet being constituted by the atomic groups (inclusive of ioncontaining groups) arranged in plane. Specifically, the layered silicate is an inorganic layered compound that is constructed by tetrahedron sheets composed of silicon atoms, aluminum atoms and oxygen atoms and octahedron sheets composed of aluminum atoms, magnesium atoms, oxygen atoms and hydrogen atoms in a ratio of 1:1 or 2:1.

Further, in addition to the above atoms, the tetrahedron sheet may contain iron atoms, and the octahedron sheet may contain iron atoms, chromium atoms, manganese atoms, nickel atoms or lithium atoms. In addition to molecules of water, cations such as potassium ion, sodium ion or calcium ion may be present as exchangeable cations between the layers of the layered silicate.

The layered silicate used in the present invention is preferably a smectite group silicate, for example, a natural layered silicate such as montmorillonite, beidellite, saponite, hectorite and sauconite which are belonging to smectite group (natural smectite). A layered silicate belonging to smectite group that is produced from an inorganic compound by hydrothermal synthesis (synthetic smectite) is also usable. Of these, preferred is the synthetic smectite.

In the oxygen detecting composition of the present invention, the addition amounts are 0.1 to 100 parts by weight, preferably 0.5 to 50 parts by weight, more preferably 1 to 10 parts by weight for the cationic surfactant, 0.001 to 10 parts by weight, preferably 0.01 to 1 part by weight for the organic colorant, and 0.01 to 200 parts by weight, preferably 0.1 to 100 parts by weight for the reducing agent, each based on one part by weight of the layered silicate.

The oxygen detecting composition of the present invention may be prepared by mixing an aqueous dispersion of the layered silicate and an aqueous solution dissolving the cationic surfactant, the organic colorant, the reducing agent and the optional basic substance.

The oxygen detecting composition of the present invention is preferably a composite material of the layered silicate intercalated with the cationic surfactant, the organic colorant, the reducing agent and the optional basic substance, although not specifically limited thereto. The intercalation of the organic colorant, etc. can be confirmed by X-ray diffraction or by the color change function attributable to the organic colorant and the reducing agent that are brought close together by the action of the intercalated cationic surfactant.

The oxygen detecting composition of the present invention may be made into a powdery oxygen detecting agent by mixing with an inorganic substance. A known inorganic substance such as zeolite may be used, and a basic inorganic substance such as magnesium carbonate is particularly preferable. The amount of the inorganic substance is preferably 50 to 500 parts by weight based on one part by weight of the layered silicate.

The mixture of the oxygen detecting composition of the present invention and the inorganic substance may be tableted into a tablet-type oxygen detecting agent. An oxygen detecting agent of film, sheet or thread shape can be obtained by impregnating a paper, cloth or thread with an alkaline aqueous solution of the oxygen detecting composition of the present invention.

The oxygen detecting agent may be also prepared in the same manner as in the production method for the conventional oxygen detecting agent except for adding the cationic surfactant and using an aqueous dispersion or solution of the solid layered silicate instead of water used in the conventional method.

The intercalation of the cationic surfactant into the layered silicate can be attained by replacing exchangeable cations present between the layers of the layered silicate with the cationic surfactant. Therefore, the cationic surfactant is used in the present invention. If the organic colorant or the reducing agent is cationic, the intercalation thereof can be effected by replacing the exchangeable cations with the organic colorant or the reducing agent. If nonionic, the intercalation of the organic colorant or the reducing agent is effected in cooperation with the cationic surfactant. The intercalation of the basic substance is effected in cooperation with the cationic surfactant.

The interlayer distance of the layered silicate is expanded by the intercalation of the cationic surfactant, organic colorant and reducing agent. The intercalation is therefore confirmed by measuring the interlayer distance, for example, by X-ray diffractometry.

The oxygen detecting composition of the present invention may be produced by mixing an aqueous dispersion of the layered silicate with an aqueous solution containing the cationic surfactant, the organic colorant, the reducing agent and the optional basic substance; removing water by filtration or centrifugation; and drying in the form of a thin film or a massive solid. Alternatively, a solid oxygen detecting composition may be produced by mixing a solid layered silicate with a solid or liquid cationic surfactant, organic colorant, reducing agent and optional basic substance using a mortar or the like. In this method, a small amount of a solvent such as water and alcohol may be added, if required. It was confirmed by X-ray diffractometry that the interlayer distance of the layered silicate contained in the oxygen detecting composition obtained in this method was expanded.

The oxygen detecting composition of the present invention may be a solid pigment and is therefore used as it is or formed into a shaped article such as film. Alternatively, the oxygen detecting composition may be dispersed in another solid material or mixed with another solid material to prepare an oxygen detecting agent in the form of tablet, sheet, film or other shapes. The oxygen detecting composition also serves as a pigment for an oxygen detecting ink, and is therefore made into an oxygen detecting ink by mixing with a solvent, a binder or the like. Letters, figures, patterns, etc. of the oxygen detecting ink can be provided on paper, plastic tape, etc. by the application or printing, thereby obtaining the oxygen detector for indicating the presence (or absence) of oxygen. In addition, by printing letters, figures, patterns, etc. with the oxygen detecting ink on the inner surface of a gas-barrier container, the surface of an oxygen absorbing package, etc., the presence or absence of oxygen within the container can be recognized from outside.

The present invention will be described in more detail below with reference to the following examples and comparative examples. However, these examples are only illustrative and not intended to limit the present invention thereto.

EXAMPLE 1

Into 20 mL of 5.0 g/L aqueous dispersion of a layered silicate (synthetic smectite, "SUMECTON SA", trade name of Kunimine Industries Co., Ltd., hereinafter simply referred to as "smectite"), was added 10 mL of aqueous solution dissolving 0.01 g of methylene blue, 1.0 g of D-(+)-glucose and 0.18 g of cetyltrimethylammonium bromide. By impregnating 25 g of magnesium carbonate with the resultant mixture, a powdery blue oxygen detecting agent was prepared.

The following color change test was conducted using the powdery blue oxygen detecting agent. The oxygen detecting agent was hermetically stored in a gas-barrier container together with a commercially available oxygen absorbing agent ("AGELESS SA", trademark of Mitsubishi Gas Chemical Company, Inc.). The oxygen concentration in the container was traced by a zirconia oxygen analyzer. The oxygen detecting agent changed its color from blue to white almost simultaneously with reaching a deoxygenated state (oxygen concentration of less than 0.1% by volume), and immediately returned its color to blue upon exposure to air by opening the container. This procedure was repeated to confirm that the color change was reversible with respect to the oxygen concentration.

EXAMPLE 2

A mixture of 20 mL of a 5.0 g/L aqueous dispersion of smectite and 5 mL of aqueous solution dissolving 0.01 g of methylene blue, 1.0 g of D-(+)-glucose and 0.36 g of cetyltrimethylammonium bromide was adjusted to pH 11.0 by adding dropwise a 0.1 N NaOH. A filter paper was impregnated with the resulting mixture to obtain a blue oxygen detecting agent of sheet type.

The oxygen detecting agent contained 1.2 mol of cetyltrimethylammonium bromide, 0.056 mol of methylene blue and 8.6 mol of D-(+)-glucose, each based on 1.0 charge equivalent of the exchangeable cations in the smectite.

Using the blue oxygen detecting agent of sheet type, the color change test was carried out in the same manner as in Example 1. The oxygen detecting agent changed its color to white almost at the same time when the inner atmosphere of the gas-barrier container became a deoxygenated state (oxygen concentration of less than 0.1% by volume), and immediately returned its color to blue upon exposure to air by opening the container. This procedure was repeated to confirm that the color change was reversible with respect to the oxygen concentration.

EXAMPLE 3

Into 15 mL of a 5.0 g/L aqueous dispersion of smectite, was added 15 mL of aqueous solution dissolving 0.03 g of methylene blue, 0.02 g of Phloxine, 2.5 g of xylose and 0.32 g of cetyltrimethylammonium chloride. After impregnating 50 g of magnesium carbonate with the mixture, the resulting powder was tableted to prepare a bluish purple oxygen detecting agent of tablet type.

Using the oxygen detecting agent thus prepared, the following accelerated light exposure test was carried out. The oxygen detecting agent was exposed to a 5000 lx visible light from a fluorescent lamp at 25° C. and 60% RH in air. The change of concentration of the organic colorant was traced by a visible spectrophotometer, and the light resistance was evaluated by the degree of change. Even after 96 h of the exposure to the fluorescent light, the peak intensity of the maximum absorption of methylene blue at about 650 nm was not decreased.

COMPARATIVE EXAMPLE 1

A commercially available oxygen detecting agent of tablet type ("AGELESS EYE C", trademark of Mitsubishi Gas Chemical Company, Inc.) was exposed to a 5000 lx visible light from a fluorescent lamp at 25° C. and 60% RH in air in the same manner as in Example 3 to carry out the accelerated light exposure test. After 96 h of starting the exposure to the fluorescent light, the peak intensity of the maximum absorption of methylene blue at about 650 nm was decreased by 25%.

EXAMPLE 4

The bluish purple oxygen detecting agent of tablet type was subjected to an accelerated heat exposure test at 60° C. and 60% RH in a deoxygenated atmosphere. Specifically, the oxygen detecting agent was placed in a gas-barrier container and hermetically stored under a deoxygenated condition (oxygen concentration of less than 0.1% by volume) at 60° C. and 60% RH. After exposing the test sample to air by opening the container, the change of concentration of the organic colorant was traced by a visible spectrophotometer, and the heat resistance was evaluated by the degree of change. Even after 10 days of starting the accelerated heat exposure test, no decrease in the peak intensity of the maximum absorption of methylene blue at about 650 nm was noticed.

COMPARATIVE EXAMPLE 2

In the same manner as in Example 4, a commercially available oxygen detecting agent of tablet type ("AGELESS EYE C", trademark of Mitsubishi Gas Chemical Company, Inc.) was placed in a gas-barrier container and stored under a deoxygenated condition at 60° C. and 60% RH to carry out the accelerated heat exposure test. After exposing the test sample to air by opening the container, the change of concentration of the organic colorant was traced by a visible spectrophotometer, and the heat resistance was evaluated by the degree of change. The peak intensity of the maximum absorption of methylene blue at about 650 nm was decreased by 10% after three days and by 17% after 10 days.

COMPARATIVE EXAMPLE 3

A tablet was prepared in the same manner as in Example 3 except for omitting the use of cetyltrimethylammonium chloride. The results of the color change test carried out in the same manner as in Example 1 taught that the tablet did not change its color to pink that indicated the deoxygenated condition even 24 h after the inner atmosphere of the gas-barrier container reached the deoxygenated condition (oxygen concentration of less than 0.1% by volume), i.e., the tablet did not show the oxygen detecting function.

EXAMPLE 5

A mixture of 20 mL of a 5.0 g/L aqueous dispersion of a layered silicate (synthetic smectite "SUMECTON SA"), 10 mL of a 0.51 mmol/L aqueous solution of methylene blue, and 5 mL of an aqueous solution dissolving 0.18 g of L-(+)-ascorbic acid and 0.18 g of cetyltrimethylammonium bromide was mixed by ultrasonic wave for 30 min and then subjected to centrifugal separation to obtain a blue translucent massive oxygen detecting agent.

The following color change test was conducted using the oxygen detecting agent thus obtained. The oxygen detecting agent was hermetically stored in a gas-barrier container together with a commercially available oxygen absorbing agent ("AGELESS SA", trademark of Mitsubishi Gas Chemical Company, Inc.). The oxygen concentration in the container was traced by a zirconia oxygen analyzer. The oxygen detecting agent turned near colorless transparent almost simultaneously with reaching a deoxygenated state (oxygen concentration of less than 0.1% by volume), and immediately returned to its original bluish transparent state upon exposure to air by opening the container. This procedure was repeated to confirm that the color change was reversible with respect to the oxygen concentration.

EXAMPLE 6

A mixture of 20 mL of a 5.0 g/L aqueous dispersion of the smectite, 10 mL of a 0.5 mmol/L aqueous solution of methylene blue, and 5 mL of an aqueous solution dissolving 0.18 g of D-(+)-glucose and 0.36 g of cetyltrimethylammonium bromide was mixed by ultrasonic wave for 30 min, and adjusted to pH 11.0 by dropping a 0.1 N NaOH. The resultant mixture was subjected to suction filtration using a membrane filter having 0.45 µm pore size to obtain a blue transparent oxygen detecting agent of thin-film type.

The obtained blue transparent oxygen detecting agent of thin-film type contained 1.2 mol of cetyltrimethylammonium bromide, 0.056 mol of methylene blue and 4.3 mol of D-(+)-glucose, each based on 1.0 charge equivalent of the exchangeable cations in the smectite.

Using the blue transparent oxygen detecting agent of thin-film type, the color change test was carried out in the same manner as in Example 1. The oxygen detecting agent turned near colorless transparent almost simultaneously with reaching a deoxygenated state (oxygen concentration of less than 0.1% by volume), and immediately returned to its original bluish transparent state upon exposure to air by opening the container. This procedure was repeated to confirm that the color change was reversible with respect to the oxygen concentration.

The interlayer distance of the oxygen detecting agent was measured as 2.60 nm by X-ray diffractometry, while 1.31 nm for the starting smectite. Since the interlayer distance was increased from 1.31 nm to 2.60 nm by the treatment with methylene blue, D-(+)-glucose and cetyltrimethylammonium bromide, it would appear that these compounds were intercalated between the layers. In an intercalation compound obtained by intercalating an organic compound between the layers of a layered silicate, the intercalated compound can be generally removed by heat treatment. By the heat treatment at 400° C. for 2 h in air, the interlayer distance of the blue transparent, thin-film oxygen detecting agent was reduced to 1.32 nm that was nearly equal to the interlayer distance of the starting smectite.

EXAMPLE 7

An aqueous dispersion (100 mL) containing 0.2 meq/L of layered silicate (synthetic smectite), 0.01 mmol/L of methylene blue, 1.0 mmol/L of cetyltrimethylammonium chloride and 2.0 mmol/l of L-(+)-ascorbic acid was filtered through a membrane filter having a diameter of 35 mm and a pore size of 0.2 µm to obtain a blue transparent oxygen detecting agent of thin-film type.

The blue transparent oxygen detecting agent of thin-film type was subjected to the following accelerated light exposure test. The oxygen detecting agent was placed on a slide glass and irradiated with a visible light of 390 nm or more from a xenon lamp. The change of concentration of the organic colorant was traced by a visible spectrophotometer, and the light resistance was evaluated by the degree of change. The peak intensity of the maximum absorption of methylene blue at about 650 nm was reduced with the exposing time to visible light, and, after 30 min of the exposure, reduced to about 50% of its initial level before starting the exposure. The luminous energy of 500 nm visible light used here was 4.14 W, and the luminous energy of visible light from a room fluorescent lamp was 0.2 mW. Therefore, the 30 min exposure to light from the xenon lamp in this example corresponded to 430-day exposure to light under ordinary room fluorescent lamps.

COMPARATIVE EXAMPLE 4

A commercially available oxygen detecting agent of tablet type ("AGELESS EYE C" trade name of Mitsubishi Gas Chemical Company, Inc.) was subjected to the same accelerated light exposure test using a visible light from a xenon lamp as in Example 3. After 5 min of the exposure to light, the concentration of the organic colorant component in "AGELESS EYE C" was reduced to about 50% of the initial concentration before exposure. Thus, the 5-min exposure to light from the xenon lamp in this example corresponded to 72-day exposure to light under ordinary room fluorescent lamps.

COMPARATIVE EXAMPLE 5

A printed oxygen detecting agent produced using an oxygen detecting ink ("PAPER EYE UYR" trademark of Mitsubishi Gas Chemical Company, Inc.) was subjected to the same accelerated light exposure test using a visible light from a xenon lamp as in Example 3. After 0.08 min of the exposure to light, the concentration of the organic colorant component in "PAPER EYE UYR" was reduced to about 50% of the initial concentration before exposure. Thus, the 0.08-min exposure to light from the xenon lamp corresponded to 1-day exposure to light under ordinary room fluorescent lamps.

EXAMPLE 8

Into a mixture of 200 mL of a 5.0 g/L aqueous dispersion of smectite, 100 mL of a 0.16 g/L aqueous solution of methylene blue and 25 mL of a 64 g/L aqueous solution of cetyltrimethylammonium chloride, was added a 1.8 g of L(+)-ascorbic acid. The resulting mixture was subjected to suction filtration using a membrane filter having a pore size of 0.45 µm to obtain a blue transparent oxygen detecting ink pigment in the form of a thin film.

The oxygen detecting ink pigment was mixed with 3.8 g of a pentaerythritol ester of rosin, 1.3 g of propylene glycol monoethyl ether, 1.3 g of mineral spirits and 2.0 g of clay to prepare an oxygen detecting ink. Blue picture symbols were screen-printed on a woodfree paper with the oxygen detecting ink. The printed paper was hermetically stored in a transparent gas-impermeable container together with an oxygen-absorbing agent ("AGELESS SAPE", trademark of Mitsubishi Gas Chemical Company, Inc.) and cotton impregnated with water. Within 3 days, the blue picture symbols changed to almost colorless, and returned to its original blue color within 40 min upon exposure to air. This indicates that the oxygen detecting ink pigment of the present invention exhibited a good printability and a good oxygen detecting function.

As described above, in accordance with the present invention, there is provided an oxygen detecting composition having a relatively high light and heat stability.

Thus, the oxygen detecting composition of the present invention is of great value as a powdery oxygen detecting agent, a tableted oxygen detecting agent, an oxygen detecting agent comprising paper, cloth or fiber impregnated with the oxygen detecting composition, or an oxygen detector applied or printed with a oxygen detecting ink containing the oxygen detecting composition, for preserving foods and maintain the quality of medical and pharmaceutical products.

Further, in accordance with the present invention, there is provided a transparent or translucent solid oxygen detecting agent, which makes the packaged content easily visible outwardly without hiding the contents therebehind.

What is claimed is:

1. An oxygen detecting composition comprising a composite material prepared by mixing, as essential components, a layered silicate, a cationic surfactant, an organic colorant and a reducing agent.

2. The oxygen detecting composition according to claim 1, wherein the cationic surfactant, the organic colorant and the reducing agent are intercalated between layers of the layered silicate.

3. The oxygen detecting composition according to claim 1, wherein the layered silicate is selected from smectite group silicates.

4. The oxygen detecting composition according to claim 1, wherein the oxygen detecting composition further comprises a basic substance.

5. An oxygen detecting agent comprising the oxygen detecting composition as defined in claim 1 and an inorganic substance.

6. The oxygen detecting agent according to claim 5, which is made into a form of tablet.

7. An oxygen detecting agent comprising paper, cloth or fiber impregnated with the oxygen detecting composition as defined in claim 1.

8. An oxygen detecting ink pigment comprising the oxygen detecting composition as defined in claim 1.

9. An oxygen detecting ink comprising the oxygen detecting composition as defined in claim 1.

10. An oxygen detector made by applying or printing the oxygen detecting ink according to claim 9 to a surface.

* * * * *